United States Patent [19]

Bundy

[11] 4,005,115

[45] Jan. 25, 1977

[54] PHENYL-SUBSTITUTED PROSTAGLANDIN-A TYPE ANALOGS

[75] Inventor: Gordon L. Bundy, Portage, Mich.

[73] Assignee: The Upjohn Company, Kalamazoo, Mich.

[22] Filed: Dec. 29, 1975

[21] Appl. No.: 645,278

Related U.S. Application Data

[60] Division of Ser. No. 431,011, Jan. 7, 1974, Pat. No. 3,987,087, which is a continuation-in-part of Ser. No. 167,446, July 29, 1971, abandoned, which is a continuation-in-part of Ser. No. 86,303, Nov. 2, 1970, abandoned.

[52] U.S. Cl. .................. 260/410.9 R; 424/305; 424/308; 260/240 R; 260/340.9; 260/343.6; 260/408; 260/410; 260/410.5; 260/413; 260/468 D; 260/473 R; 260/473 A; 260/456 NS; 260/520 B; 260/586 R

[51] Int. Cl.$^2$ .................. C07C 5/22; C07C 69/76
[58] Field of Search ............... 260/410.9 R, 473 A, 260/520 B, 410, 410.5, 413

[56] References Cited

FOREIGN PATENTS OR APPLICATIONS 2,154,309   4/1972   Germany ................... 260/473 A

*Primary Examiner*—Paul J. Killos

[57] ABSTRACT

This invention is a group of phenyl-substituted PGE-type, PGF-type, PGA-type and PGB-type compounds, and processes for making them. These compounds are useful for a variety of pharmacological purposes, including anti-ulcer, inhibition of platelet aggregation, increase of nasal patency, labor inducement at term, and wound healing.

105 Claims, No Drawings

PHENYL-SUBSTITUTED PROSTAGLANDIN-A TYPE ANALOGS

CROSS REFERENCE TO RELATED APPLICATIONS

This is a division of application Ser. No. 431,011, filed Jan. 7, 1974 which is a continuation-in-part of my copending application Ser. No. 167,446, filed July 29, 1971 now abandoned, which in turn is a continuation-in-part of my application Ser. No. 86,303, filed Nov. 2, 1970, now abandoned.

DESCRIPTION OF THE INVENTION

This invention relates to compositions of matter, and to methods and intermediates for producing them. The several aspects of this invention relate to novel analogs of some of the known prostaglandins, for example, prostaglandin $E_1$ ($PGE_1$, prostaglandin $E_2$ ($PGE_2$), prostaglandin $F_1$ ($PGF_1 \beta$ and $PGF_1 \beta$ ), prostaglandin $F_2$ ($PGF_2 \alpha$ and $PGF_2 \beta$ ), prostaglandin $A_1$ ($PGA_1$), prostaglandin $A_2$ ($PGA_2$), prostaglandin $B_1$ ($PGB_1$), prostaglandin $B_2$ ($PGB_2$), and the dihydro derivatives of $PGE_1$, $PGF_1 \alpha$, $PGA_1$, and $PGB_1$, to novel methods for producing those novel prostaglandin analogs, and to novel chemical intermediates useful in those novel methods. In particular, the novel prostaglandin analogs of this invention are phenyl-substituted in the C-13 to C-20 chain.

The essential material for this application, including the background of the invention, the disclosure of the invention, and the description of the preferred embodiments, including Preparations and Examples, is incorporated by reference from pending and commonly owned U.S. Patent Application Ser. No. 431,011, filed Jan. 7, 1974, now U.S. Pat. 3,987,087, under the provisions of M.P.E.P. 608.01(p).

SUMMARY OF THE INVENTION

It is the purpose of this invention to provide novel prostaglandin analogs, and processes for making them.

The novel prostaglandin analogs of this invention each have a benzene ring as part of the C-13 to C-20 chain of the prostanoic acid structure (I) acid or 8-isoprostanoic acid structure (VII). That benzene ring is present as a substituted or unsubstituted phenyl moiety (1) attached as a substituent replacing one of the hydrogens on one of the methylenes between C-15 and the terminal methyl of the prostanoic acid or 8-isoprostanoic acid structure or (2) attached to the terminal or omega carbon of the C-16 to C-20 portion of the chain, replacing either (a) one of the hydrogens of the terminal methyl, (b) the entire terminal methyl, or (c) the terminal methyl plus one to four of the methylenes adjacent to that terminal methyl. In Formulas IX and X, "trinor" and "dinor" indicate absence of the terminal $-CH_2-CH_2-CH_3$ and the terminal $-CH_2-CH_3$, respectively, of $PGE_1$ and $PGF_2$. The words "nor", "dinor", "trinor", "tetranor", and "pentanor" in the names given here and hereinafter for novel prostaglandins of this invention are to be construed as indicating the number of carbon atoms, i.e. one, 2, 3, 4 or 5, missing from the C-16 to C-20 position of the prostanoic acid carbon skeleton. The phenyl or substituted phenyl moiety is attached to the remaining portion of the prostanoic acid skeleton, i.e., to C-19 for the nor-compounds, to C-18 for the dinor compounds, to C-17 for the trinor compounds, to C-16 for the tetranor compounds, and to C-15 for the pentanor compounds. In addition, the term can include carbon atoms missng from the C-1 to C-7 position of the prostanoic acid skeleton, for example, 17-phenyl-2,18,19,20-tetranor $PGF_2$.

Some of the novel prostaglandin analogs of this invention differ structurally in other ways from the known prostanoic acid derivatives, having, for example, more or fewer carbon atoms in the C-1 to C-7 chain of prostanoic acid, and having one or more alkyl and/or fluoro substituents in that chain or in the C-13 to C-20 chain of prostanoic acid.

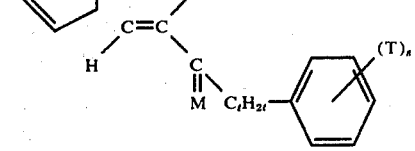

XIX

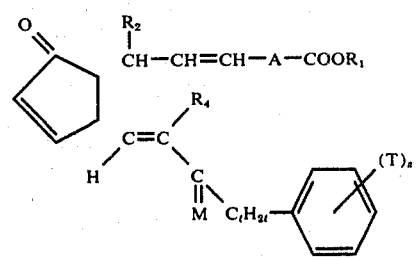

XX

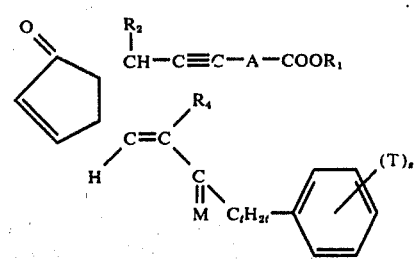

XXI

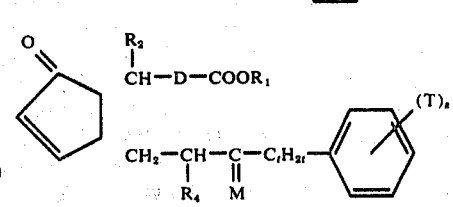

XXII

In Formulas XIX to XXII, $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2 or 3 chloro or alkyl of one to 4 carbon atoms, inclusive, or ethyl substituted in the β-position with 3 chloro, 2 or 3 bromo, or 1, 2, or 3 iodo. M is

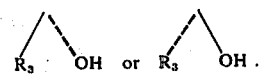

$R_2$, $R_3$, and $R_4$ are hydrogen or alkyl of one to 4 carbon atoms, inclusive. The moiety $-C_tH_{2t}-$ represents (a) a valence bond or (b) alkylene of one to 10 carbon atoms, inclusive, substituted with zero, one, or 2 fluoro, with one to 7 carbon atoms, inclusive, between

and the ring. When one or 2 fluoro are present as substituents of —C$_t$H$_{2t}$, that moiety will contain 2t-1 or 2t-2 hydrogen atoms, respectively, rather than 2t hydrogen atoms. The symbol T represents alkyl of one to 4 carbon atoms, inclusive, fluoro, chloro, trifluoromethyl, or —OR$_9$, wherein R$_9$ is hydrogen or alkyl of one to 4 carbon atoms, inclusive. The symbol s represents zero, one, 2, or 3. Regarding the combination (T)$_s$ attached to the phenyl ring, no more than two T's are other than alkyl. Except for that proviso, when two or three T's are present as substituents, they are the same or different. The symbol D represents alkylene of 3 to 12 carbon atoms, inclusive, substituted with zero, one, 2, 3, or 4 fluoro, with 3 to 7 carbon atoms, inclusive, between —CHR$_2$— and COOR$_1$, and with the proviso that when 3 or 4 fluoro are present, they are all substituents of the carbon atoms alpha and beta to COOR$_1$. The symbol A represents alkylene of one to 10 carbon atoms, inclusive, substituted with zero, one, 2, 3, or 4 fluoro, with one to 5 carbon atoms, inclusive, between =CH— or     C— and —COOR$_1$, and with the proviso that when 3 or 4 fluoro are present, they are all substituents of the carbon atoms alpha and beta to —COOR$_1$.

The wavy line ~ in Formulas XIX to XXII indicates attachment of the hydroxyl or the side chain to the cyclopentane ring in alpha or beta configuration.

Formulas XIX to XXII include the separate isomers wherein M is either

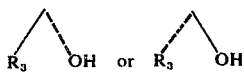

i.e. where the side chain hydroxy is in either S (alpha) or R (epi or beta) configuration. Referring to the prostanoic acid atom numbering (formula I above), the point of attachment corresponds to C–15, and, herein regardless of the variation in the C–1 to C–7 carbon chain, these epimers are referred to as C–15 epimers.

Included in Formula are both the cis and the trans compounds with respect to the C–5 to C–6 carbon-carbon double bond in the carboxyl-terminated side chain. In all of the compounds containing the C–13 to C–14 double bond, that carbon-carbon double bond is in trans configuration, and the chain containing R$_4$ is attached to the cyclopentane ring in beta configuration in compounds encompassed by Formulas XI to XXII.

Formulas XIX to XXII include lower alkanoates, and also pharmacologically acceptable salts when R$_1$ is hydrogen.

Like the natural prostaglandins described above, these novel phenyl-substituted prostaglandin compounds have several centers of asymmetry. The novel compounds of this invention include (a) compounds having the same configurations as naturally occurring prostaglandins and (b) racemic compounds of (a) plus optically active enantiomeric forms thereof. As discussed hereinabove, two structural formulas are required to define accurately these racemic compounds.

Formulas XIX through XXII, inclusive, are intended to represent optically active prostanoic acid analogs having the same absolute configuration as the naturally-occurring prostaglandins.

The embodiments of the invention in which an exclusive property or privilege is claimed are defined as follows:

1. An optically active compound of the formula:

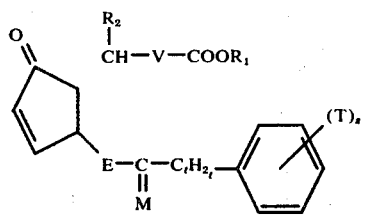

or a racemic compound of that formula and the mirror image thereof, wherein E is —CH$_2$CHR$_4$— or trans —CH=CR$_4$—; wherein R$_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro; wherein M is

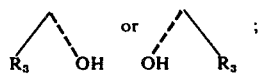

wherein R$_2$, R$_3$ and R$_4$ are hydrogen or alkyl or one to 4 carbon atoms, inclusive; wherein C$_t$H$_{2t}$ represents a valence bond or alkylene of one to 10 carbon atoms, inclusive, substituted with zero, one, or 2 fluoro, with one to 7 carbon atoms, inclusive, between

and the phenyl ring; wherein T is alkyl of one to 4 carbon atoms, inclusive, fluoro, chloro, trifluoromethyl, or —OR$_9$, wherein R$_9$ is hydrogen, or alkyl of one to 4 carbon atoms, inclusive, and s is zero, one, 2, or 3, with the proviso that not more than two T's are other than alkyl; wherein V is (a) alkylene of 3 to 12 carbon atoms, inclusive, substituted with zero, one, 2, 3, or 4 fluoro, with 3 to 7 carbon atoms, inclusive, between —CHR$_2$— and COOR$_1$, with the proviso that when 3 or 4 fluoro are present, they are all substituents of the carbon atoms alpha and beta to —COOR$_1$, (b) —CH=CH—A—, cis or trans, or (c) —C     C—A—, wherein A is alkylene of one to 10 carbon atoms, inclusive, substituted with zero, one, 2, 3, or 4 fluoro, with one to 5 carbon atoms, inclusive, between =CH— (or     C—) and —COOR$_1$, with the proviso that when 3 or 4 fluoro are present, they are all substituents of the carbon atoms alpha and beta to —COOR$_1$, with the further proviso that when E is —CH$_2$—CHR$_4$— V is (a) above; including the lower alkanoates thereof, and the pharmacologically acceptable salts thereof when R$_1$ is hydrogen.

2. 2a,2b-Dihomo-17-phenyl-18,19,20-trinor-PGA$_2$, a compound according to claim 1.

3. 2a,2b-Dihomo-17-phenyl-18,19,20-trinor-PGA$_2$, methyl ester, a compound according to claim 1.

4. A compound according to claim 1 wherein R$_2$ and R$_4$ are hydrogen, and wherein V is (a) —(CH$_2$)$_a$—X—, (b) —CH=CH—(CH$_2$)$_b$—X—, or (C) —C≡C—(CH$_2$)$_b$—X—, wherein $a$ is one, 2, 3, 4, or 5, $b$ is zero, one, 2, or 3, and X is ethylene substituted by one, 2, 3, or 4 fluoro, methyl, or ethyl, or by one alkyl of 3 or 4 carbon atoms.

5. A compound according to claim 4 wherein $a$ is 3 and $b$ is one.

6. 2,2-Difluoro-17-phenyl-18,19,20-trinor-PGA$_2$, methyl ester, a compound according to claim 5.

7. 15(S)-15-Methyl-2,2-difluoro-17-phenyl-18,19,20-trinor-PGA$_2$, methyl ester, a compound according to claim 5.

8. A compound according to claim 1 wherein R$_2$ and R$_4$ are hydrogen, and wherein V is (a) alkylene of 3 to 12 carbon atoms, inclusive, substituted with zero, one, 2, 3, or 4 fluoro, with 5 carbon atoms in the chain between —CHR$_2$— and —COOR$_1$, (b) —CH=CH—A—, cis or trans, or (c) —C≡C—A—, wherein A is alkylene of one to 10 carbon atoms, inclusive, substituted with zero, one, 2, 3, or 4 fluoro, with 3 carbon atoms in the chain between =CH— (or ≡C—) and —COOR$_1$.

9. A compound according to claim 8 wherein C$_t$H$_{2t}$ is limited to one to 4 carbon atoms in the chain between

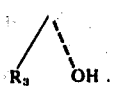

and the phenyl ring.

10. A compound according to claim 9 wherein V is alkylene of 3 to 12 carbon atoms, inclusive, substituted with zero, one, 2, 3, or 4 fluoro, with 5 carbon atoms in the chain between —CHR$_2$— and —COOR$_1$; and wherein E is trans —CH=CH—.

11. A compound according to claim 10 wherein M is

12. A compound according to claim 11 wherein R$_3$ is hydrogen.

13. A compound according to claim 12 wherein C$_t$H$_{2t}$ is ethylene.

14. A compound according to claim 13 wherein R$_1$ is hydrogen, and the pharmacologically acceptable salts thereof.

15. 17-Phenyl-18,19,20-trinor-PGA$_1$, a compound according to claim 14.

16. A compound according to claim 13 wherein R$_1$ is alkyl of one to 8 carbon atoms, inclusive.

17. 17-Phenyl-18,19,20-trinor-PGA$_1$, methyl ester, a compound according to claim 16.

18. A compound according to claim 12 wherein C$_t$H$_{2t}$ is

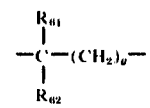

wherein $g$ is zero, one, 2, or 3, and wherein R$_{61}$ and R$_{62}$ are hydrogen, alkyl of one to 4 carbon atoms, inclusive, or fluoro, only when R$_{61}$ is hydrogen or fluoro, and with the further proviso that R$_{61}$ and R$_{62}$ are not both hydrogen.

19. A compound according to claim 18 wherein R$_{61}$ and R$_{62}$ are alkyl of one to 4 carbon atoms, inclusive.

20. A compound according to claim 19 wherein C$_t$H$_{2t}$ is —C(CH$_3$)$_2$—CH$_2$—.

21. A compound according to claim 20 wherein R$_1$ is hydrogen, and the pharmacologically acceptable salts thereof.

22. 16,16-Dimethyl-17-phenyl-18,19,20-trinor—PGA$_2$, a compound according to claim 21.

23. A compound according to claim 20 wherein R$_1$ is alkyl of one to 8 carbon atoms, inclusive.

24. 16,16-Dimethyl-17-phenyl-18,19,20-trinor-PGA$_1$, methyl ester, a compound according to claim 23.

25. A compound according to claim 12 wherein C$_t$H$_{2t}$ is trimethylene.

26. A compound according to claim 25 wherein R$_1$ is hydrogen, and the pharmacologically acceptable salts thereof.

27. 18-Phenyl-19,20,-dinor-PGA$_1$, a compound according to claim 26.

28. A compound according to claim 25 wherein R$_1$ is alkyl of one to 8 carbon atoms, inclusive.

29. 18-Phenyl-19,20-dinor-PGA$_1$, methyl ester, a compound according to claim 28.

30. A compound according to claim 11 wherein R$_3$ is methyl.

31. A compound according to claim 30 wherein C$_t$H$_{2t}$ is ethylene.

32. A compound according to claim 31 wherein R$_1$ is hydrogen, and the pharmacologically acceptable salts thereof.

33. 15(S)-15-Methyl-17-phenyl-18,19,20-trinor-PGA$_1$, a compound according to claim 32.

34. A compound according to claim 31 wherein R$_1$ is alkyl of one to 8 carbon atoms, inclusive.

35. 15(S)-15-Methyl-17-phenyl-18,19,20-trinor-PGA$_1$, methyl ester, a compound according to claim 34.

36. A compound according to claim 30 wherein C$_t$H$_{2t}$ is trimethylene.

37. A compound according to claim 36 wherein R$_1$ is hydrogen, and the pharmacologically acceptable salts thereof.

38. 15(S)-15-Methyl-18-phenyl-19,20-dinor-PGA$_1$, a compound according to claim 37.

39. A compound according to claim 36 wherein R$_1$ is alkyl of one to 8 carbon atoms, inclusive.

40. 15(S)-15-Methyl-18-phenyl-19,20-dinor-PGA$_1$, a compound according to claim 39.

41. A compound according to claim 10 wherein M is

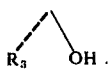

42. A compound according to claim 41 wherein $R_3$ is hydrogen.

43. A compound according to claim 41 wherein $R_3$ is methyl.

44. A compound according to claim 43 wherein $C_tH_{2t}$ is ethylene.

45. A compound according to claim 44 wherein $R_1$ is hydrogen, and the pharmacologically acceptable salts thereof.

46. 15(R)-15-Methyl-17-phenyl-18,19,20-trinor-PGA$_1$, a compound according to claim 45.

47. A compound according to claim 44 wherein $R_1$ is alkyl of one to 8 carbon atoms, inclusive.

48. 15(R)-15-Methyl-17-phenyl-18,19,20-trinor-PGA$_1$, methyl ester, a compound according to claim 47.

49. A compound according to claim 9 wherein V is —CH=CH—A—, cis or trans, wherein A is alkylene of one to 10 carbon atoms, inclusive, substituted with zero, one, 2, 3, or 4 fluoro, with 3 carbon atoms in the chain between =CH— and —COOR$_1$; and wherein E is trans—CH=CH—.

50. A compound according to claim 49 wherein M is

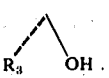

51. A compound according to claim 50 wherein $R_3$ is hydrogen.

52. A compound according to claim 51 wherein $C_tH_{2t}$ is ethylene.

53. A compound according to claim 52 wherein $R_1$ is hydrogen, and the pharmacologically acceptable salts thereof.

54. 17-Phenyl-18,19,20-trinor-PGA$_2$, a compound according to claim 53.

55. 17-(p-Chlorophenyl)-18,19,20-trinor-PGA$_2$, a compound according to claim 53.

56. 17-(p-Fluorophenyl)-18,19,20-trinor-PGA$_2$, a compound according to claim 53.

57. A compound according to claim 52 wherein $R_1$ is alkyl of one to 8 carbon atoms, inclusive.

58. 17-Phenyl-18,19,20-trinor-PGA$_2$, methyl ester, a compound according to claim 57.

59. 17-(p-Chlorophenyl)-18,19,20-trinor-PGA$_2$, methyl ester, a compound according to claim 57.

60. 17-(p-Chlorophenyl)-18,19,20-trinor-PGA$_2$, ethyl ester, a compound according to claim 57.

61. A compound according to claim 51 wherein $C_tH_{2t}$ is

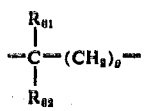

wherein $g$ is zero, one, 2, or 3, and wherein $R_{61}$ and $R_{62}$ are hydrogen, alkyl of one to 4 carbon atoms, inclusive, or fluoro, being the same or different, with the proviso that $R_{62}$ is fluoro only when $R_{61}$ is hydrogen or fluoro, and with the further proviso that $R_{61}$ and $R_{62}$ are not both hydrogen.

62. A compound according to claim 61 wherein $R_{61}$ and $R_{62}$ are alkyl of one to 4 carbon atoms, inclusive.

63. A compound according to claim 62 wherein $C_tH_{2t}$ is —C(CH$_3$)$_2$—CH$_2$—.

64. A compound according to claim 63 wherein $R_1$ is hydrogen, and the pharmacologically acceptable salts thereof.

65. 16,16-Dimethyl-17-phenyl-18,19,20-trinor-PGA$_2$, a compound according to claim 64.

66. A compound according to claim 63 wherein $R_1$ is alkyl of one to 8 carbon atoms, inclusive.

67. 16,16-Dimethyl-17-phenyl-18,19,20-trinor-PGA$_2$, methyl ester, a compound according to claim 66.

68. A compound according to claim 51 wherein $C_tH_{2t}$ is trimethylene.

69. A compound according to claim 68 wherein $R_1$ is hydrogen, and the pharmacologically acceptable salts thereof.

70. 18-Phenyl-19,20-dinor-PGA$_2$, a compound according to claim 69.

71. A compound according to claim 68 wherein $R_1$ is alkyl of one to 8 carbon atoms, inclusive.

72. 18-Phenyl-19,20-dinor-PGA$_2$, methyl ester, a compound according to claim 71.

73. A compound according to claim 50 wherein $R_3$ is methyl.

74. A compound according to claim 73 wherein $C_tH_{2t}$ is ethylene.

75. A compound according to claim 74 wherein $R_1$ is hydrogen, and the pharmacologically acceptable salts thereof.

76. 15(S)-15-Methyl-17-phenyl-18,19,20-trinor-PGA$_2$, a compound according to claim 75.

77. A compound according to claim 74 wherein $R_1$ is alkyl of one to 8 carbon atoms, inclusive.

78. 15(S)-15-Methyl-17-phenyl-18,19,20-trinor-PGA$_2$, methyl ester, a compound according to claim 77.

79. A compound according to claim 73 wherein $C_tH_{2t}$ is trimethylene.

80. A compound according to claim 79 wherein $R_1$ is hydrogen, and the pharmacologically acceptable salts thereof.

81. 15(S)-15-Methyl-18-phenyl-19,20-dinor-PGA$_2$, a compound according to claim 80.

82. A compound according to claim 79 wherein $R_1$ is alkyl of one to 8 carbon atoms, inclusive.

83. 15(S)-15-Methyl-18-phenyl-19,20-dinor-PGA$_2$, methyl ester, a compound according to claim 82.

84. A compound according to claim 49 wherein M is

85. A compound according to claim 84 wherein $R_3$ is hydrogen.

86. A compound according to claim 84 wherein $R_3$ is methyl.

87. A compound according to claim 86 wherein $C_tH_{2t}$ is ethylene.

88. A compound according to claim 87 wherein $R_1$ is hydrogen, and the pharmacologically acceptable salts thereof.

89. 15(R)-15-Methyl-17-phenyl-18,19,20-trinor-PGA$_2$, a compound according to claim 88.

90. A compound according to claim 87 wherein R$_1$ is alkyl of one to 8 carbon atoms, inclusive.

91. 15(R)-15-Methyl-17-phenyl-18,19,20-trinor-PGA$_2$, methyl ester, a compound according to claim 90.

92. A compound according to claim 9 wherein V is —C≡C—A—, wherein A is alkylene of one to 10 carbon atoms, inclusive, substituted with zero, one, 2, 3, or 4 fluoro, with 3 carbon atoms in the chain between ≡C— and —COOR$_1$; and wherein E is trans—CH=CH—.

93. A compound according to claim 9 wherein V is alkylene of 3 to 12 carbon atoms, inclusive, substituted with zero, one, 2, 3, or 4 fluoro, with 5 carbon atoms in the chain between —CHR$_2$— and —COOR$_1$; and wherein E is —CH$_2$CH$_2$—.

94. A compound according to claim 93 wherein M is

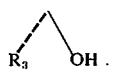

95. A compound according to claim 94 wherein R$_3$ is hydrogen.

96. A compound according to claim 95 wherein C$_t$H$_{2t}$ is ethylene.

97. A compound according to claim 96 wherein R$_1$ is hydrogen, and the pharmacologically acceptable salts thereof.

98. 13,14-Dihydro-17-phenyl-18,19,20-trinor-PGA$_1$, a compound according to claim 97.

99. A compound according to claim 96 wherein R$_1$ is alkyl of one to 8 carbon atoms, inclusive.

100. 13,14-Dihydro-17-phenyl-18,19,20-trinor-PGA$_1$, methyl ester, a compound according to claim 99.

101. A compound according to claim 94 wherein R$_3$ is methyl.

102. A compound according to claim 101 wherein C$_t$H$_{2t}$ is ethylene.

103. A compound according to claim 102 wherein R$_1$ is hydrogen, and the pharmacologically acceptable salts thereof.

104. 13,14-Dihydro-15(S)-15-methyl-17-phenyl-18,19,20-trinor-PGA$_1$, a compound according to claim 103.

105. A compound according to claim 93 wherein M is

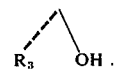

* * * * *

UNITED STATES PATENT OFFICE
CERTIFICATE OF CORRECTION

Patent No. 4,005,115   Dated January 25, 1977

Inventor(s) Gordon L. Bundy

It is certified that error appears in the above-identified patent and that said Letters Patent are hereby corrected as shown below:

Column 1, line 20, "$PGF_1\beta$ and $PGF_1\beta$" should read -- $PGF_1\alpha$ and $PGF_1\beta$ --.

Column 1, line 24, "$PGF_1\alpha$, $PGA_1$" should read -- $PGF_1\alpha$, $PGF_1\beta$, $PGA_1$ --.

Column 1, line 58, "$PGF_2$ ." should read -- $PGF_2\alpha$. --.

Column 2, line 5, "$PGF_2$ ." should read -- $PGF_2\alpha$. --.

Column 2, line 13, "    " should read -- Each of the novel phenyl-substituted prostaglandin analogs of this invention is encompassed by one of the following formulas or by the combination of that formula and its mirror image --.

Column 2, lines 16-18, formula XIX should appear as shown below instead of as in the patent

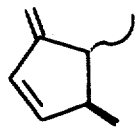

Column 2, lines 26-28, formula XX should appear as shown below instead of as in the patent

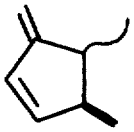

UNITED STATES PATENT OFFICE
CERTIFICATE OF CORRECTION

Patent No. 4,005,115  Dated January 25, 1977

Inventor(s) Gordon L. Bundy

It is certified that error appears in the above-identified patent and that said Letters Patent are hereby corrected as shown below:

Column 2, lines 37-39, formula XXI should appear as shown below instead of as in the patent

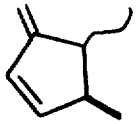

Column 2, lines 47-49, formula XXII should appear as shown below instead of as in the patent

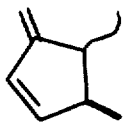

Column 3, line 28, "C-" should read -- ≡C- --.

Column 3, line 48, "Formula are" should read -- Formula XX are --.

Column 4, lines 12-13, claim 1, should appear as shown below instead of as in the patent

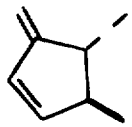

Column 4, line 56, "-C C-A-" should read -- -C≡C-A- --.

Column 4, line 60, "C-)" should read -- ≡C-) --

Column 5, line 6, "(C)" should read -- (c) --.

Column 5, line 23, "-CH=λCH-A-" should read -- -CH=CH-A- -- .

Column 5, line 24, "-C C-" should read -- -C≡C- --.

UNITED STATES PATENT OFFICE
CERTIFICATE OF CORRECTION

Patent No. 4,005,115      Dated January 25, 1977

Inventor(s) Gordon L. Bundy

It is certified that error appears in the above-identified patent and that said Letters Patent are hereby corrected as shown below:

Column 5, line 27, "or C-)" should read -- or $\equiv$C-) --.

Column 6, line 22, "$PGA_2$" should read -- $PGA_1$ --.

Column 9, line 13, "C-", should read -- $\equiv$C- --.

Column 9, line 10, "-C C-" should read -- -C$\equiv$C- --.

Column 9, lines 23-27, "$R_3$   OH" should read -- $R_3$   OH --.

Signed and Sealed this

Seventh Day of February 1978

[SEAL]

Attest:

RUTH C. MASON
*Attesting Officer*

LUTRELLE F. PARKER
*Acting Commissioner of Patents and Trademarks*